United States Patent [19]

Ramanadin et al.

[11] 4,351,777

[45] Sep. 28, 1982

[54] PREPARATION OF FLUOROBENZONITRILES

[75] Inventors: R. Ramanadin; Alain Roustan, both of Ales; Gerard Soula, Meyzieu, all of France

[73] Assignee: Rhone-Poulenc Industries, Paris, France

[21] Appl. No.: 304,627

[22] Filed: Sep. 22, 1981

[30] Foreign Application Priority Data

Sep. 25, 1980 [FR] France ................................ 80 20573

[51] Int. Cl.³ .......................................... C07C 121/52
[52] U.S. Cl. .............................................. 260/465 G
[58] Field of Search ..................................... 260/465 G

[56] References Cited

U.S. PATENT DOCUMENTS 3,290,353 12/1966 Battershell et al. ............ 260/465 G
4,229,365 10/1980 Oeser et al. ................. 260/465 G X Primary Examiner—Dolph H. Torrence
Attorney, Agent, or Firm—Burns, Doane, Swecker & Mathis

[57] ABSTRACT

Fluorobenzonitriles are prepared by reacting their corresponding chlorobenzonitriles with at least one alkali metal fluoride, in an aprotic solvent reaction medium, in the presence of at least one tertiary amine sequestering agent having the structural formula:

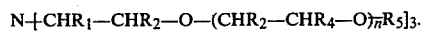

$$N + CHR_1 - CHR_2 - O - (CHR_2 - CHR_4 - O)_{\overline{n}} R_5]_3.$$

13 Claims, No Drawings

PREPARATION OF FLUOROBENZONITRILES

BACKGROUND OF THE INVENTION

1. Field of the Invention

The present invention relates to the preparation of fluorobenzonitriles, and, more espcially, to the preparation of fluorobenzonitriles from their corresponding chlorobenzonitriles by reaction of the latter with an alkali metal fluoride.

2. Description of the Prior Art

It is known to this art to prepare fluorobenzonitriles by the reaction of chlorobenzonitriles with an alkali metal fluoride, such as potassium fluoride, in aprotic solvents, such as, for example, dimethylformamide, dimethylsulfone and sulfone (see, for example, British patent specification No. 2,016,000), optionally in the presence of a catalyst, such as cesium fluoride (see French Pat. No. 2,391,990).

Yet the known reactions proceed far too slowly to be of significant value on an industrial scale.

SUMMARY OF THE INVENTION

Accordingly, a major object of the present invention is the provision of an improved process for the preparation of fluorobenzonitriles, which process can be conducted much more rapidly vis-a-vis those known to the art, is more valuable on an industrial scale, and is far more productive in the preparation of those fluorobenzonitriles useful as intermediates in the preparation of various phytosanitary compounds and pharmaceuticals.

Briefly, the present invention features a process for the preparation of fluorobenzonitriles by reacting their corresponding chlorobenzonitriles with at least one alkali metal fluoride, in an aprotic solvent reaction medium, in the presence of at least one tertiary amine sequestering agent having the structural formula:

$$N\!\!-\!\![CHR_1\!\!-\!\!CHR_2\!\!-\!\!O\!\!-\!\!(CHR_3\!\!-\!\!CHR_4\!\!-\!\!O)_{\overline{n}}R_5]_3 \quad (I)$$

wherein n is a number greater than or equal to 0 and less than or equal to about 10 ($0 \leq n \leq 10$), $R_1$, $R_2$, $R_3$, $R_4$, which may be identical or different, each represents a hydrogen atom or an alkyl radical having from 1 to 4 carbon atoms and $R_5$ represents an alkyl or cycloalkyl radical having from 1 to 12 carbon atoms, a phenyl radical or a radical of the formula $-C_mH_{2m}-$, or $C_mH_{2m+1}-\phi-$, with m ranging from 1 to about 12 and $\phi$ being phenyl.

DETAILED DESCRIPTION OF THE INVENTION

More particularly according to this invention, in a preferred embodiment thereof, a sequestering agent of the formula (I) is used in which $R_1$, $R_2$, $R_3$ and $R_4$ represent a hydrogen atom or a methyl radical, $R_5$ and n being as above-defined.

Among such sequestering agents, it is even more particularly preferred to use those in which n is greater than or equal to 0 and less than or equal to 6 and in which $R_5$ represents an alkyl radical having from 1 to 4 carbon atoms.

The following sequestering agents are noted as illustrative:

[1] tris-(3-oxabutyl)-amine of the formula:

[2] tris-(3,6-dioxaheptyl)-amine of the formula:

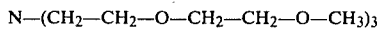

[3] tris-(3,6,9-trioxadecyl)-amine of the formula:

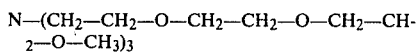

[4] tris-(3,6-dioxaoctyl)-amine of the formula:

$$N\!\!-\!\!(CH_2\!\!-\!\!CH_2\!\!-\!\!O\!\!-\!\!CH_2\!\!-\!\!CH_2\!\!-\!\!O\!\!-\!\!C_2H_5)_3$$

[5] tris-3,6,9-trioxaundecyl)-amine of the formula:

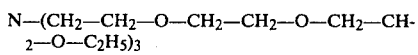

[6] tris-(3,6-dioxanonyl)-amine of the formula:

$$N\!\!-\!\!(CH_2\!\!-\!\!CH_2\!\!-\!\!O\!\!-\!\!CH_2\!\!-\!\!CH_2\!\!-\!\!O\!\!-\!\!C_3H_7)_3$$

[7] tris-(3,6,9-trioxadodecyl)-amine of the formula:

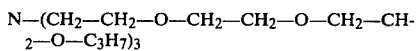

[8] tris-(3,6-dioxadecyl)-amine of the formula:

$$N\!\!-\!\!(CH_2\!\!-\!\!CH_2\!\!-\!\!O\!\!-\!\!CH_2\!\!-\!\!CH_2\!\!-\!\!O\!\!-\!\!C_4H_9)_3$$

[9] tris-(3,6,9-trioxatridecyl)-amine of the formula:

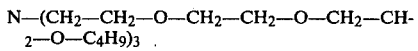

[10] tris-(3,6,9,12-tetraoxatridecyl)-amine of the formula:

$$N\!\!-\!\!(CH_2\!\!-\!\!CH_2\!\!-\!\!O\!\!-\!\!(CH_2\!\!-\!\!CH_2\!\!-\!\!O)_3\!\!-\!\!CH_3)_3$$

[11] tris-(3,6,9,12,15,18-hexaoxanonadecyl)-amine of the formula:

$$N\!\!-\!\!(CH_2\!\!-\!\!CH_2\!\!-\!\!O\!\!-\!\!(CH_2\!\!-\!\!CH_2\!\!-\!\!O)_5\!\!-\!\!CH_3)_3$$

[12] tris-(3,6-dioxa-4-methylheptyl)-amine of the formula:

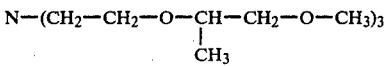

and [13] tris-(3,6-dioxa-2,4-dimethylheptyl)-amine of the formula:

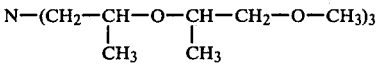

The amine sequestering agents utilized in the process according to the invention are per se known to the prior art. Thus, French Pat. No. 1,302,365 describes the preparation of the tertiary amines $N\!\!-\!\!(CH_2\!\!-\!\!CH_2\!\!-\!\!O\!\!-\!\!CH_3)_3$ and $N\!\!-\!\!(CH_2\!\!-\!\!CH_2\!\!-\!\!O\!\!-\!\!CH_2\!\!-\!\!CH_2\!\!-\!\!O\!\!-\!\!CH_3)_3$ as by-products from the synthesis of the corresponding primary and secondary amines, such primary and secondary amines being valuable as intermediates in the synthesis of various pharmaceuticals, as corrosion inhibitors, as intermediates in the synthesis of agricultural chemicals, and as emulsifiers. It will also be appreciated, though, that the prior art, including the aforenoted French Pat. No. 1,302,365, is conspicuously devoid of any suggestion that the topic amines could be utilized in any reaction within the ambit of this invention.

The fluorobenzonitriles advantageously prepared according to this invention have the structural formula:

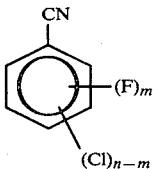

wherein n and m are integers greater than or equal to 1 and less than or equal to 5.

The subject fluorobenzonitriles are prepared from chlorobenzonitriles having the structural formula:

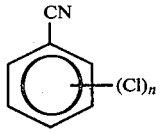

wherein n is as above defined.

The more preferred fluorobenzonitriles according to the present invention are those in which n and m are greater than or equal to 1 and less than or equal to 3, and wherein the fluorine atoms are in the ortho- and/or para-position.

The following are exemplary: 2-fluorobenzonitrile, 4-fluorobenzonitrile, 2,6-difluorobenzonitrile, 2,4-difluorobenzonitrile, 2-fluoro-6-chlorobenzonitrile, 4-fluoro-3-chlorobenzonitrile, 2-fluoro-3-chlorobenzonitrile, respectively obtained from 2-chlorobenzonitrile, 4-chlorobenzonitrile, 2,6-dichlorobenzonitrile, 3,4-dichlorobenzonitrile and 2,3-dichlorobenzonitrile. It will of course be appreciated that the chlorobenzonitriles employed in the process of the invention may comprise, in addition, substituents that are inert under the conditions of the reaction, such as the $CF_3$ and alkyl radicals, for example.

The alkali metal fluorides that may be employed within the scope of the present invention, principally, are potassium fluoride and/or cesium fluoride and/or rubidium fluoride. The alkali metal fluorides must be used in their anhydrous form.

The solvent is preferably selected from among N-methylpyrrolidone, dimethylsulfoxide, dimethylformamide and sulfolane.

Sulfolane is particularly preferred.

The selection of the sequestering agent most suitable for any particular embodiment of the invention is made by taking into consideration the size of the alkali metal cation of the alkali metal fluoride used. The greater the size of the cation, the larger the number of oxygen atoms contained in the molecule of the sequestering agent must be.

Thus, when potassium fluoride is used, for example, it is preferred to employ as the sequestering agent, tris-(3,6,9-trioxadecyl)-amine, and/or tris-(3,6,9-trioxaundecyl)-amine.

The process according to the invention is preferably carried out at a temperature between 180° C. and approximately 250° C., the temperature decreasing with increasing numbers of chlorine atoms in the starting material chlorobenzonitrile.

It is preferred to conduct the subject process at atmospheric pressure, even though pressures higher or lower than atmospheric are not excluded from the scope of the invention.

The sequestering agent is used in amounts such that the molar ratio of the sequestering agent to the alkali metal fluoride ranges from approximately 0.005 to approximately 0.2. Even more preferably, this ratio ranges from 0.01 to 0.1.

The amount of the alkali metal fluoride to be used obviously depends upon the number of chlorine atoms to be replaced by fluorine. Preferably, the reaction is carried out with a 10 to 50 molar % excess, with respect to stoichiometry.

Preferably, an amount of solvent is used such that the molar ratio of the solvent to the starting material chlorobenzonitrile ranges from approximately 1 to approximately 50, and preferably ranges from approximately 2 to approximately 20.

Reaction times typically range from approximately 3 hours to 24 hours.

In order to further illustrate the present invention and the advantages thereof, the following specific examples are given, it being understood that same are intended only as illustrative and in nowise limitative.

EXAMPLE 1

Preparation of para-fluorobenzonitrile from para-chlorobenzonitrile

Into a three-necked, 500 ml flask, equipped with a mechanical agitator, a condenser and a thermometer, the following ingredients were successively introduced:
(i) 250 g Sulfolane (2 moles), anhydrous;
(ii) 13.7 g Para-chlorobenzonitrile (0.1 mole);
(iii) 6.4 g Anhydrous potassium fluoride (0.11 mole); and
(iv) 4.6 g Tris-(3,6,9-trioxadecyl)-amine (0.01 mole).

The reaction mixture was heated to 220° C. under agitation for 24 hours, then was cooled and filtered.

Analysis by gas chromatography of the organic phase reveals 72% para-fluorobenzonitrile and 28% unconverted para-chlorobenzonitrile.

Comparative Experiment

In the absence of tris-(3,6,9-trioxadecyl)-amine, under the same operating conditions as above, after 24 hours at 220° C., the composition of the mixture was 51% para-fluorobenzonitrile and 49% unconverted 2,6-dichlorobenzonitrile.

EXAMPLE 2

Preparation of 2,6-difluorobenzonitrile from 2,6-dichlorobenzonitrile

Into an 0.5 liter, three-necked flask equipped with agitation means, a condenser and a thermometer, there were introduced:
(i) 260 g Anhydrous sulfolane;
(ii) 63.8 g Dry potassium fluoride (1.1 mole);
(iii) 68.7 g 2,6-Dichlorobenzonitrile (0.4 mole); and
(iv) 4.5 g Tris-(3,6,9-trioxadecyl)-amine (0.01 mole).

The reaction mixture was heated under agitation to 210° C. After 3 hours, 20 min. of reaction at 210° C., the chromatographic analysis of the reaction mixture yielded the following composition:
(1) 2,6-Dichlorobenzonitrile=1%
(2) 2-Fluoro-6-chlorobenzonitrile=17.4%
(3) 2,6-Difluorobenzonitrile=81.6%, and after 5 hours, 30 min. of reaction at 210° C., the composition was:
(1) 2,6-Dichlorobenzonitrile <0.1%
(2) 2-Fluoro-6-chlorobenzonitrile=4.7%
(3) 2,6-Difluorobenzonitrile=95.3%.

The products were separated by conventional means.

Comparative Experiment

When operating under the same conditions as above, but without the tris-(3,6,9-trioxadecyl)-amine, after 3 hours, 30 min. of reaction, the composition was:
(1) 2,6-Dichlorobenzonitrile=3%
(2) 2-Fluoro-6-chlorobenzonitrile=30%
(3) 2,6-Difluorobenzonitrile=67%, and after 5 hours, 30 min. of reaction, the composition was:
(1) 2,6-Dichlorobenzonitrile <0.1%
(2) 2-Fluoro-6-chlorobenzonitrile=15%
(3) 2,6-Difluorobenzonitrile=85%.

EXAMPLE 3

Preparation of 2,6-difluorobenzonitrile from 2,6-dichlorobenzonitrile

Into the apparatus described in Example 2, there were introduced:
(i) 215 g N-methyl-2-pyrrolidone (2.17 moles);
(ii) 68.75 g 2,6-Dichlorobenzonitrile (0.40 mole);
(iii) 63.8 g KF (1.1 mole); and
(iv) 4.5 g Tris-(3,6,9-trioxadecyl)-amine (0.01 mole).

The reaction mixture was heated under agitation to 210° C.

After 3 hours, 30 min. of reaction, the chromatographic analysis of the mixture obtained the yields:
(1) 2,6-Dichlorobenzonitrile: 2%
(2) 2-Fluoro-6-chlorobenzonitrile: 32%
(3) 2,6-Difluorobenzonitrile: 66%.

After 5 hours, 30 min. of reaction, the composition was:
(1) 2,6-Difluorobenzonitrile: 0.3%
(2) 2-Fluoro-6-chlorobenzonitrile: 16%
(3) 2,6-Difluorobenzonitrile: 83.7%.

Comparative Experiment

When operating as above, but without the tris-(3,6,9-trioxadecyl)-amine, the following were obtained after 3 hours, 30 min.:
(1) 2,6-Dichlorobenzonitrile: 5%
(2) 2-Fluoro-6-chlorobenzonitrile: 45%
(3) 2,6-Difluorobenzonitrile: 50%.

After 5 hours, 30 min., the composition was:
(1) 2,6-Dichlorobenzonitrile: 2%
(2) 2-Fluoro-6-chlorobenzonitrile: 28%
(3) 2,6-Difluorobenzonitrile: 70%.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A process for the preparation of a fluorobenzonitrile, comprising reacting the chlorobenzonitrile corresponding thereto with at least one alkali metal fluoride, in an aprotic solvent reaction medium, in the presence of an effective amount of at least one tertiary amine sequestering agent having the structural formula:

$$N\text{-}[CHR_1\text{-}CHR_2\text{-}O\text{-}(CHR_2\text{-}O)_{\overline{n}}R_5]_3 \quad (I)$$

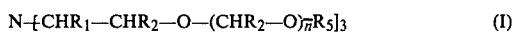

wherein n is a number greater than or equal to 0 and less than or equal to about 10, $R_1$, $R_2$, $R_3$, $R_4$, which may be identical or different, each represents a hydrogen atom or an alkyl radical having from 1 to 4 carbon atoms and $R_5$ represents an alkyl or cycloalkyl radical having from 1 to 12 carbon atoms, a phenyl radical or a radical of the formula $-C_mH_{2m}-\phi$, or $C_mH_{2m+1}-\phi-$, with m ranging from 1 to about 12 and $\phi$ being phenyl.

2. The process as defined by claim 1, wherein the formula (I), $R_1$, $R_2$, $R_3$ and $R_4$ are each hydrogen or methyl.

3. The process as defined by claims 1 or 2, wherein the formula (I), n is an integer which is greater than or equal to 0 and less than or equal to 6.

4. The process as defined by claims 1 or 2, wherein the formula (I), $R_5$ is an alkyl radical having from 1 to 4 carbon atoms.

5. The process as defined by claims 1 or 2, wherein the formula (I), $R_1$, $R_2$, $R_3$ and $R_4$, which are identical or different, are each hydrogen or methyl, n is an integer which is greater than or equal to 0 and less than or equal to 6 and $R_5$ is an alkyl radical having from 1 to 4 carbon atoms.

6. The process as defined by claim 5, wherein the tertiary amine of the formula (I) is tris-(3,6,9-trioxadecyl)-amine of the formula:

$$N\text{-}(CH_2\text{-}CH_2\text{-}O\text{-}CH_2\text{-}CH_2\text{-}O\text{-}CH_2\text{-}CH_2\text{-}O\text{-}CH_3)_3.$$

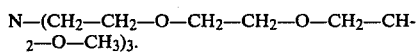

7. The process as defined by claim 5, wherein the tertiary amine of the formula (I) is tris-(3,6,9-trioxaundecyl)-amine of the formula:

$$N\text{-}(CH_2\text{-}CH_2\text{-}O\text{-}CH_2\text{-}CH_2\text{-}O\text{-}CH_2\text{-}CH_2\text{-}O\text{-}C_2H_5)_3.$$

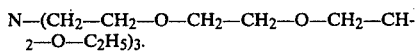

8. The process as defined by claim 1, wherein the tertiary amine of the formula (I) is selected from the group consisting of tris-(3-oxabutyl)-amine, tris-(3,6-dioxaheptyl)-amine, tris-(3,6,9-trioxadecyl)-amine, tris-(3,6-dioxaoctyl)-amine, tris-(3,6,9-trioxaundecyl)-amine, tris-(3,6-dioxanonyl)-amine, tris-(3,6,9-trioxadodecyl)-amine, tris-(3,6-dioxadecyl)-amine, tris-(3,6,9-trioxatridecyl)-amine, tris-(3,6,9,12-tetraoxatridecyl)-amine, tris-(3,6,9,12,15,18-hexaoxanonadecyl)-amine, tris-(3,6-dioxa-4-methylheptyl)-amine, and tris-(3,6-dioxa-2,4-dimethylheptyl)-amine.

9. The process as defined by claim 1, wherein the at least one alkali metal fluoride is potassium fluoride, cesium fluoride and/or rubidium fluoride.

10. The process as defined by claim 1, said aprotic solvent being N-methylpyrrolidone, dimethylsulfoxide, dimethylformamide, or sulfolane.

11. The process as defined by claim 1, the molar ratio of sequestering agent to alkali metal fluoride ranging from about 0.005 to about 0.2.

12. The process as defined by claim 11, said ratio ranging from about 0.01 to about 0.1.

13. The process as defined by claim 1, the product fluorobenzonitrile having the structural formula:
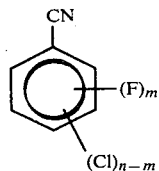
wherein n and m are integers ranging from 1 to 5.
* * * * *